(12) United States Patent
Lee et al.

(10) Patent No.: US 12,274,760 B2
(45) Date of Patent: Apr. 15, 2025

(54) METHOD FOR PREPARING FLUORINE-18-LABELED FLUOROMETHYL-SUBSTITUTED RADIOPHARMACEUTICALS USING SELECTIVE AZIDE SUBSTITUTION REACTION AND PRECURSOR SCAVENGING

(71) Applicant: Byung Chul Lee, Hanam-si (KR)

(72) Inventors: Byung Chul Lee, Hanam-si (KR); Ying Qing Lu, Guangdong (CN); Byeong Min Jo, Seoul (KR)

(73) Assignee: BIK THERAPEUTICS INC., Seoul (KR)

( * ) Notice: Subject to any disclaimer, the term of this patent is extended or adjusted under 35 U.S.C. 154(b) by 967 days.

(21) Appl. No.: 17/206,979

(22) Filed: Mar. 19, 2021

(65) Prior Publication Data

US 2021/0205482 A1    Jul. 8, 2021

Related U.S. Application Data

(63) Continuation of application No. PCT/KR2019/002862, filed on Mar. 13, 2019.

(30) Foreign Application Priority Data

Sep. 21, 2018   (KR) .................. 10-2018-0113473

(51) Int. Cl.
*A61K 51/04*   (2006.01)
(52) U.S. Cl.
CPC .......... *A61K 51/0402* (2013.01); *A61K 51/04* (2013.01)

(58) Field of Classification Search
None
See application file for complete search history.

(56) References Cited

FOREIGN PATENT DOCUMENTS

| JP | 5595903 B2 | 9/2014 |
|---|---|---|
| KR | 10-2014-0069001 A | 6/2014 |
| KR | 10-2014-0076575 A | 6/2014 |
| KR | 10-2014-0113622 A | 9/2014 |

OTHER PUBLICATIONS

Sijbom, H. et al., "Luminescent Behavior of the K2SiF6:Mn4+ Red Phosphor at High Fluxes and at the Microscopic Level," CS Journal of Solid State Science and Technology, vol. 5 (1): R3040-R3048 (2016).

*Primary Examiner* — Jake M Vu
(74) *Attorney, Agent, or Firm* — Sughrue Mion, PLLC

(57) ABSTRACT

A method for preparing a fluorine-18-labeled fluoromethyl-substituted radiopharmaceutical using a selective azide substitution reaction includes (1) obtaining a [$^{18}$F]fluoride from a cyclotron through an $^{18}$O(p,n)$^{18}$F reaction; (2) separating the [$^{18}$F] fluoride using an acetonitrile reaction solution containing dissolved $K_{2,2,2}$ and $K_2CO_3$ to obtain a [$^{18}$F]F$^-$/H$_2^{18}$O solution; (3) heating the [$^{18}$F]F$^-$/H$_2^{18}$O solution to obtain $K_{2,2,2}$/K$^{18}$F; (4) placing the $K_{2,2,2}$/K$^{18}$F along with a bis(tosyloxy)methane compound into a reactor and adding a reaction solvent to cause a reaction and obtain a first precursor solution; (5) cooling the first precursor solution and adding an azide reagent to cause an azide substitution reaction and obtain a [$^{18}$F]fluoromethyltosylate compound; (6) adding a bioactive molecule to the [$^{18}$F]fluoromethyltosylate compound to cause an alkylation reaction and obtain a second precursor solution; and (7) adding a precursor scavenger to the second precursor solution and scavenging unreacted precursors to produce a fluorine-18-labeled fluoromethyl-substituted radiopharmaceutical.

8 Claims, 9 Drawing Sheets

METHOD FOR PREPARING FLUORINE-18-LABELED FLUOROMETHYL-SUBSTITUTED RADIOPHARMACEUTICALS USING SELECTIVE AZIDE SUBSTITUTION REACTION AND PRECURSOR SCAVENGING

CROSS-REFERENCE TO RELATED APPLICATIONS

This application is a Continuation of International Patent Application No. PCT/KR2019/002862 filed on Mar. 13, 2019, which claims priority to Korean Patent Application No. KR 10-2018-0113473 filed on Sep. 21, 2018, which applications are incorporated herein by reference in their entireties.

TECHNICAL FIELD

The present invention relates to a method for preparing a [$^{18}$F]fluoromethyl-substituted radiopharmaceutical using a selective azide substitution reaction and, more particularly, to a method for preparing a fluorine-18-labeled fluoromethyl-substituted radiopharmaceutical using a selective azide substitution reaction and precursor scavenging that reduces the manufacturing time and cost and maintain a high labeling yield through a selective azide substitution reaction and precursor scavenging on unreacted precursors in the synthesis of a fluorine-18-labeled fluoromethyl-substituted radiopharmaceutical and produces a radiopharmaceutical with high purity and high quality while avoiding an HPLC (High Performance Liquid Chromatography) separation process almost necessary to the synthesis of radiopharmaceuticals.

BACKGROUND ART

Position emission tomography (PET) is an imaging technique mainly used in nuclear medicine to visualize the distribution and activity of a radiopharmaceutical injected into the body, thereby non-invasively providing information on the diagnosis and treatment effect of diseases. Fluorine-18 is a radioisotope most widely used in PET due to its adequate half-life (110 minutes) and reactivity. There are two methods of manufacturing a fluorine-18-labeled radiopharmaceutical: using a late-stage radiofluorination reaction to label a target compound having bioactivity with fluorine-18 in the last stage of the labeling reaction; and using a fluorine-18-labeled building block to effectively introduce fluorine-18 to a target compound.

The late-stage radiofluorination method to label a target compound with fluorine-18 in the last stage of the labeling reaction has been used in the past ten years to overcome the limitations of the fluorine-18 labeling reaction, but still has limitations such as the instability of precursors, complexity of the synthesis, and time spent in the separation and purification process. For this reason, studies have been conducted on the method of using a building block as an alternative to the fluorine-18 labeling reaction, since using a building block has the advantage that the building block can be purchased and readily synthesized. In addition, the development of a fluorine-18-labeled building block with high labeling yield and high purity through a simplified method under appropriate conditions has a great advantage in terms of the extensibility of use that allows introduction of fluorine-18 to a variety of bioactive molecules using the building block.

In particular, the late-stage radiofluorination method to label a target compound with fluorine-18 in the last stage of the labeling reaction is not applicable to [$^{18}$F]fluorocholine (for tumor imaging), [$^{18}$F]fluoromethyl triphenylphosphonium cations (for cardiac imaging) and S-[$^{18}$F]fluoroalkylated diarylguanidine (N-methyl-D-aspartate receptor) among the previously developed radiopharmaceuticals and reported radioactive tracers due to the chemical problem in association with the synthesis and stability of precursors. The only strategic labeling method in these cases is manufacturing fluorine-18-labeled radiopharmaceuticals using a building block.

Among the fluorine-18-labeled building blocks, a [$^{18}$F] fluoromethyl group can be introduced to the elements such as oxygen, nitrogen, phosphorus, and sulfur in the bioactive molecule, altering the structure of the existing compound to a minimum extent and minimizing the change in the chemical and biological properties of the existing compound. For this reason, various radiopharmaceuticals and candidate substances have a structural characteristic in which a [$^{18}$F] fluoromethyl group and deuterium are introduced by substitution using a fluorine-18-labeled building block, as shown in FIG. 1.

[$^{18}$F]fluoromethyl bromide is a typical building block currently used for a substitution reaction of the [$^{18}$F]fluoromethyl group in the manufacture of radiopharmaceuticals. But, the [$^{18}$F]fluoromethyl bromide is difficult to handle in the fluorine-18-labeling reaction because of its low boiling point (19° C.) and thus high volatility and badly bound to cause in vivo exposure and a high loss of labeling yield. In an attempt to overcome these shortcomings, in 2005, the Neal group developed [$^{18}$F]fluoromethyltosylate in which fluorine-18 is incorporated into the one tosyl group in bis(tosyloxy)methane. Relative to the [$^{18}$F]fluoromethyl bromide, the [$^{18}$F]fluoromethyltosylate building block has low volatility, so it allows a separation process using HPLC and a yield of fluorine-18 label 70% or higher. Furthermore, in order to improve the in vivo stability of the [$^{18}$F] fluoromethyltosylate, [$^{18}$F]fluoromethyltosylate-d$_2$ was developed by incorporating fluorine-18 into bis(tosyloxy) methane-d$_2$ in which deuterium was substituted for the hydrogen of the methyl group. When such a [$^{18}$F]fluoromethyltosylate compound is used in the subsequent substitution reaction without an HPLC separation and purification process, it is inevitable to produce the target radiopharmaceutical with side reactions and low yield due to excess bis(tosyloxy)methane present in the reactant. Here, bis(tosyloxy)methane, a fluorine-18 label precursor is present in a small amount of the μmol level, yet far higher in concentration than [$^{18}$F]fluoromethyltosylate which is to be used in the subsequent substitution reaction. As a result, using the [$^{18}$F]fluoromethyl group in bioactive molecules without an HPLC separation process can cause the excess bis(tosyloxy) methane precursor to adversely affect the final separation process as well as the final yield of the radiopharmaceutical synthesis.

Accordingly, at least one HPLC separation process is necessary to the production of a [$^{18}$F]fluoromethyl-incorporated radiopharmaceutical according to the conventional method. It is required to perform an HPLC separation in order to obtain pure [$^{18}$F]fluoromethyltosylate and, in some cases, another HPLC separation process after incorporation of the [$^{18}$F]fluoromethyltosylate into the bioactive molecule. The HPLC separation process in the production of a radiopharmaceutical causes not only a hassle in the preparation process (requiring at least 30 minutes), but a long labeling time (another 30 minutes or longer) and a low labeling yield, leading to many limitations in the production process of radiopharmaceuticals under GMP requirements.

In consequence, there is a demand for a production method for radiopharmaceuticals that overcomes the problems with the HPLC separation process and enables an effective labeling with fluorine-18 through shortened labeling and separation processes.

SUMMARY

Accordingly, the present invention has been made to solve the above problems occurring in the prior art, and an object of the present invention is to provide a method for preparing a radiopharmaceutical that is useful in labeling with fluorine-18 (F-18) having a longer half-life than C-11.

Another object of the present invention is to provide a method for preparing a [$^{18}$F]fluoromethyltosylate compound ([$^{18}$F]fluoromethyltosylate or deuterium-substituted [$^{18}$F]fluoromethyltosylate-$d_2$) as a building block that allows inactivating only the reactive precursor of a bis(tosyloxy)methane compound (bis(tosyloxy)methane or deuterium-substituted bis(tosyloxy)methane-$d_2$) presented after incorporation of fluorine-18 using a selective azide substitution reaction in order to omit an HPLC separation process necessary to the synthesis of radiopharmaceuticals and induces a high labeling yield of the target radiopharmaceutical in the subsequent substitution reaction.

Still another object of the present invention is to provide a method for preparing a radiopharmaceutical that can synthesize a fluorine-18-labeled radiopharmaceutical with high purity by using a precursor scavenger (guanidine-based heterocyles, isocyanates) and performing a separation on a cartridge in order to avoid an HPLC separation process which is necessary to the synthesis of radiopharmaceuticals having a [$^{18}$F]fluoromethyltosylate compound ([$^{18}$F]fluoromethyltosylate or deuterium-substituted [$^{18}$F]fluoromethyltosylate-$d_2$) as a substituent in the subsequent stage.

In accordance with an aspect of the present invention for achieving the object of the present invention, there is provided a method for preparing a fluorine-18-labeled fluoromethyl-substituted radiopharmaceutical using a selective azide substitution reaction that includes: (1) obtaining a [$^{18}$F]fluoride from a cyclotron through an $^{18}$O (p,n)$^{18}$F reaction; (2) separating the [$^{18}$F] fluoride using an acetonitrile reaction solution containing dissolved $K_{2,2,2}$ and $K_2CO_3$ to obtain a [$^{18}$F]F$^-$/H$_2$$^{18}$O solution; (3) heating the [$^{18}$F]F$^-$/H$_2$$^{18}$O solution to obtain $K_{2,2,2}$/K$^{18}$F; (4) placing the $K_{2,2,2}$/K$^{18}$F along with a bis(tosyloxy)methane compound into a reactor and adding a reaction solution to cause a reaction and obtain a first precursor solution; (5) cooling the first precursor solution and adding an azide compound to cause an azide substitution reaction selectively on the bis(tosyloxy)methane compound present in the first precursor solution and obtain a [$^{18}$F]fluoromethyltosylate compound; (6) adding a bioactive molecule to the [$^{18}$F]fluoromethyltosylate compound to cause an alkylation reaction and obtain a second precursor solution; and (7) adding a precursor scavenger to the second precursor solution and scavenging unreacted precursors to produce a pure fluorine-18-labeled fluoromethyl-substituted radioligand or a fluorine-18-labeled fluoromethyl-substituted radioligand using a mixed solvent of water and an organic solvent without a separate HPLC separation process when the product obtained after scavenging the unreacted precursors contains a quaternary amine.

The step (2) of obtaining the [$^{18}$F]F$^-$/H$_2$$^{18}$O solution may be performed on a Chromafix-HCO$_3$ cartridge or a quaternary methyl ammonium (QMA) anion exchange cartridge.

The step (3) of obtaining the $K_{2,2,2}$/K$^{18}$F may be performed at temperatures of 50 to 180° C. in the nitrogen gas atmosphere.

The step (4) of obtaining the first precursor solution may be performed by placing the $K_{2,2,2}$/K$^{18}$F along with a bis(tosyloxy)methane compound into a reactor and adding a reaction solution to cause a reaction at 80 to 180° C. for 1 to 30 minutes.

The azide reagent may be an azide-containing compound. The azide-containing compound may be tetrabutyl azide (nBu$_n$NH$_3$), sodium azide (NaN$_3$), potassium azide (KN$_3$), or lithium azide (LiN$_3$).

The azide substitution reaction of the step (5) may be performed at 40 to 100° C. for 2 to 10 minutes.

In the step (6) of obtaining the second precursor solution, the alkylation reaction may be an O-, N-, S-, P-alkylation reaction.

The step (5) of obtaining the [$^{18}$F]fluoromethyltosylate compound may further include performing a cartridge separation process using a cartridge packed with C18-substituted silica, or move on to the step (6) without performing the cartridge separation process.

The step (6) of obtaining the second precursor solution after the selective azide substitution reaction may be performed using an O-, N-, S-, P-alkylation reaction, or using a mixed solvent of water and an organic solvent when the product of the alkylation reaction contains a quaternary amine.

The precursor scavenger may be a scavenger selected from the group consisting of guanidine-based heterocycles and isocyanates.

The method may further include performing a cartridge separation of the fluorine-18-labeled fluoromethyl-substituted radiopharmaceutical on a cartridge packed with silica or C18-substituted silica to increase the purity of the fluorine-18-labeled fluoromethyl-substituted radiopharmaceutical.

The cartridge separation step may be performed using a mixed solvent including at least two solvents.

The method may be performed on an automated synthesis device and a cassette system.

The method for preparing a fluorine-18-labeled fluoromethyl-substituted radiopharmaceutical using a selective azide substitution reaction according to the present invention can provide a preparation process capable of selectively performing an azide substitution reaction only on an excess bis(tosyloxy)methane compound during a reaction of an azide and the two tosylate compounds (the excess bis(tosyloxy)methane compound and a trace of [$^{18}$F]fluoromethyltosylate compound) present in the crude mixture after the labeling of the bis(tosyloxy)methane compound with fluorine-18 and stably maintaining the fluorine-18-labeled [$^{18}$F]fluoromethyltosylate compound, and avoid an HPLC separation process necessary to the production of a fluorine-18-labeled fluoromethyl-substituted radiopharmaceutical through a separation process for scavenging the bioactive molecules used in the subsequent alkylation reaction, thereby producing a GMP-grade radiopharmaceutical with high purity and high quality while reducing the manufacturing time and cost for the radiopharmaceutical and maintaining a high labeling yield.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
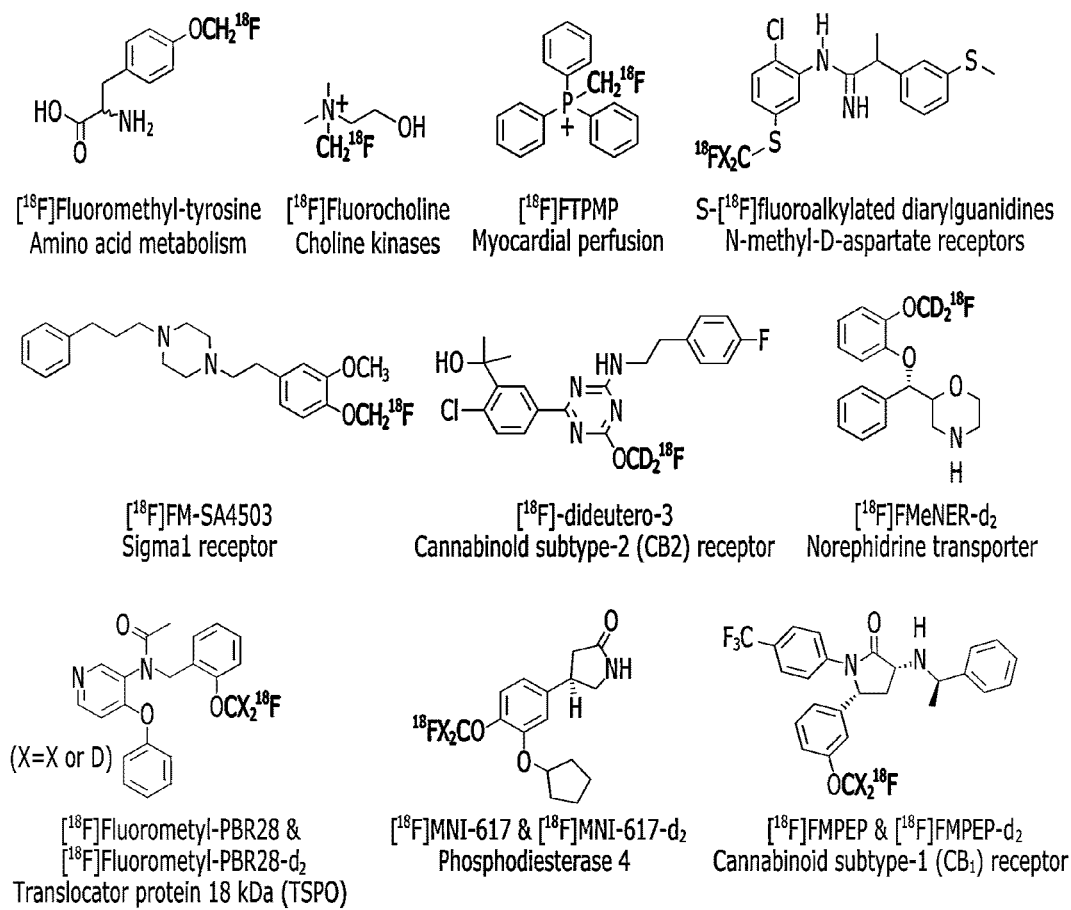
FIG. 1 illustrates the chemical structures of fluorine-18-labeled fluoromethyl-substituted radiopharmaceuticals that can be produced by the synthesis of a [$^{18}$F]fluoromethyltosylate compound according to the embodiment of the present invention.

In order to achieve the objects of the present invention, there is provided a method for preparing a fluorine-18-labeled fluoromethyl-substituted radiopharmaceutical using a selective azide substitution reaction according to the present invention that comprises: (1) obtaining a [$^{18}$F] fluoride from a cyclotron through an $^{18}$O (p,n)$^{18}$F reaction; (2) separating the [$^{18}$F] fluoride using an acetonitrile reaction solution containing dissolved K$_{2,2,2}$ and K$_2$CO$_3$ to obtain a [$^{18}$F]F$^-$/H$_2$$^{18}$O solution; (3) heating the [$^{18}$F]F$^-$/H$_2$$^{18}$O solution to obtain K$_{2,2,2}$/K$^{18}$F; (4) placing the K$_{2,2,2}$/K$^{18}$F along with a bis(tosyloxy)methane compound into a reactor and adding a reaction solution to cause a reaction and obtain a first precursor solution; (5) cooling the first precursor solution and adding an azide compound to cause an azide substitution reaction selectively on the bis (tosyloxy)methane compound present in the first precursor solution and obtain a [$^{18}$F]fluoromethyltosylate compound; (6) adding a bioactive molecule to the [$^{18}$F]fluoromethyltosylate compound to cause an alkylation reaction and obtain a second precursor solution; and (7) adding a precursor scavenger to the second precursor solution and scavenging unreacted precursors to produce a pure fluorine-18-labeled fluoromethyl-substituted radioligand or a fluorine-18-labeled fluoromethyl-substituted radioligand using a mixed solvent of water and an organic solvent without a separate HPLC separation process when the product obtained after scavenging the unreacted precursors contains a quaternary amine.

The step (2) of obtaining the [$^{18}$F]F$^-$/H$_2$$^{18}$O solution may be performed on a Chromafix-HCO$_3$ cartridge or a quaternary methyl ammonium (QMA) anion exchange cartridge.

The step (3) of obtaining the K$_{2,2,2}$/K$^{18}$F may be performed at temperatures of 50 to 180° C. in the nitrogen gas atmosphere.

The step (4) of obtaining the first precursor solution may be performed by placing the K$_{2,2,2}$/K$^{18}$F along with a bis(tosyloxy)methane compound into a reactor and adding a reaction solution to cause a reaction at 80 to 180° C. for 1 to 30 minutes.

The azide reagent may be an azide-containing compound. The azide-containing compound may be tetrabutyl azide (nBu$_n$NH$_3$), sodium azide (NaN$_3$), potassium azide (KN$_3$), or lithium azide (LiN$_3$).

The azide substitution reaction of the step (5) may be performed at 40 to 100° C. for 2 to 10 minutes.

In the step (6) of obtaining the second precursor solution, the alkylation reaction may be an O-, N-, S-, P-alkylation reaction.

The step (5) of obtaining the [$^{18}$F]fluoromethyltosylate compound may further include performing a cartridge separation process using a cartridge packed with C18-substituted silica, or move on to the step (6) without performing the cartridge separation process.

The step (6) of obtaining the second precursor solution after the selective azide substitution reaction may be performed using an O-, N-, S-, P-alkylation reaction, or using a mixed solvent of water and an organic solvent when the product of the alkylation reaction contains a quaternary amine.

The precursor scavenger may be a scavenger selected from the group consisting of guanidine-based heterocycles and isocyanates.

The method may further include performing a cartridge separation of the fluorine-18-labeled fluoromethyl-substituted radiopharmaceutical on a cartridge packed with silica or C18-substituted silica to increase the purity of the fluorine-18-labeled fluoromethyl-substituted radiopharmaceutical.

The cartridge separation step may be performed using a mixed solvent including at least two solvents.

The method may be performed on an automated synthesis device and a cassette system.

The terminologies used in this disclosure and the claims are to be interpreted to have meanings and concepts coinciding with the technical conceptions of the present invention on the basis of the principle that the concepts of the terms can be properly defined by the inventors for the sake of the best explanation of the present invention.

Hereinafter, the present invention will be described in further detail. However, it is to be noted that the present invention is not limited to the embodiments as disclosed herein but can be embodied in various other ways. The embodiments of the present invention are given to make the disclosure of the present invent complete and enable those skilled in the related art to completely understand the scope of the present invention.

Figure 2:
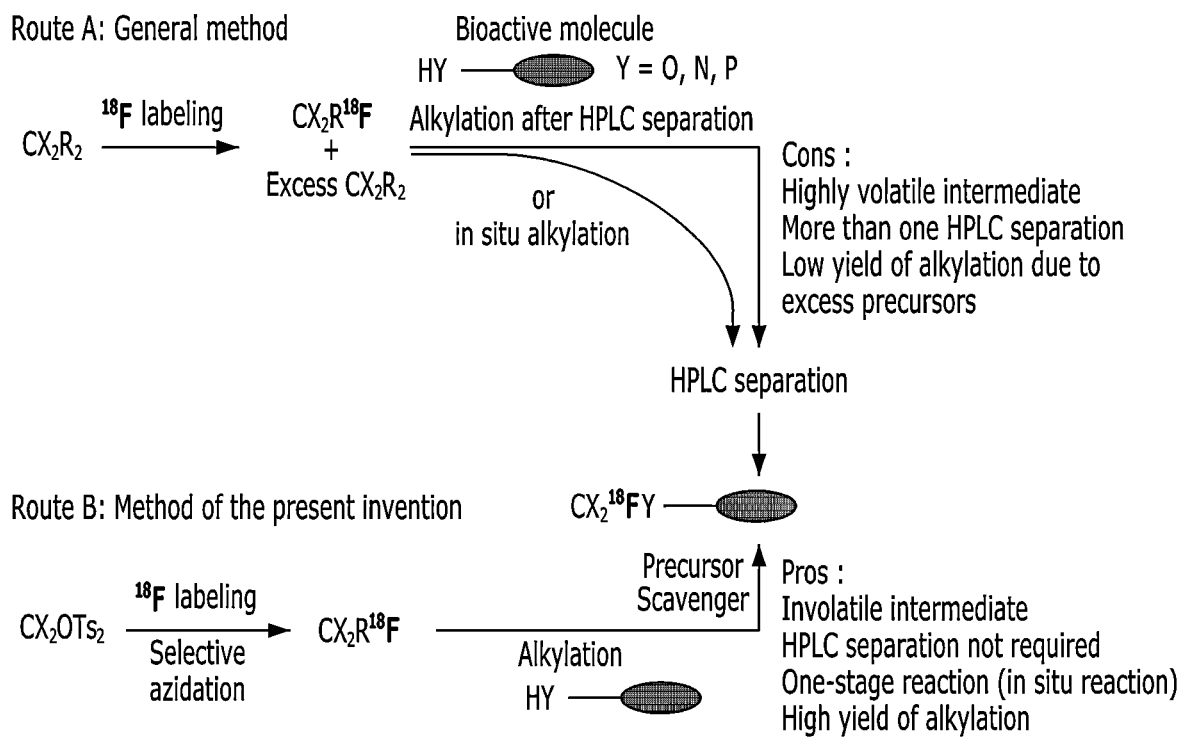
FIG. 2 illustrates the schemes for a preparation method B for fluorine-18-labeled fluoromethyl-substituted radiopharmaceutical using the synthesis of a [$^{18}$F]fluoromethyltosylate compound through a selective azide substitution reaction and precursor scavenging and a conventional preparation method A for fluorine-18-labeled fluoromethyl-substituted radiopharmaceutical requiring an HPLC separation process.
Figure 3:
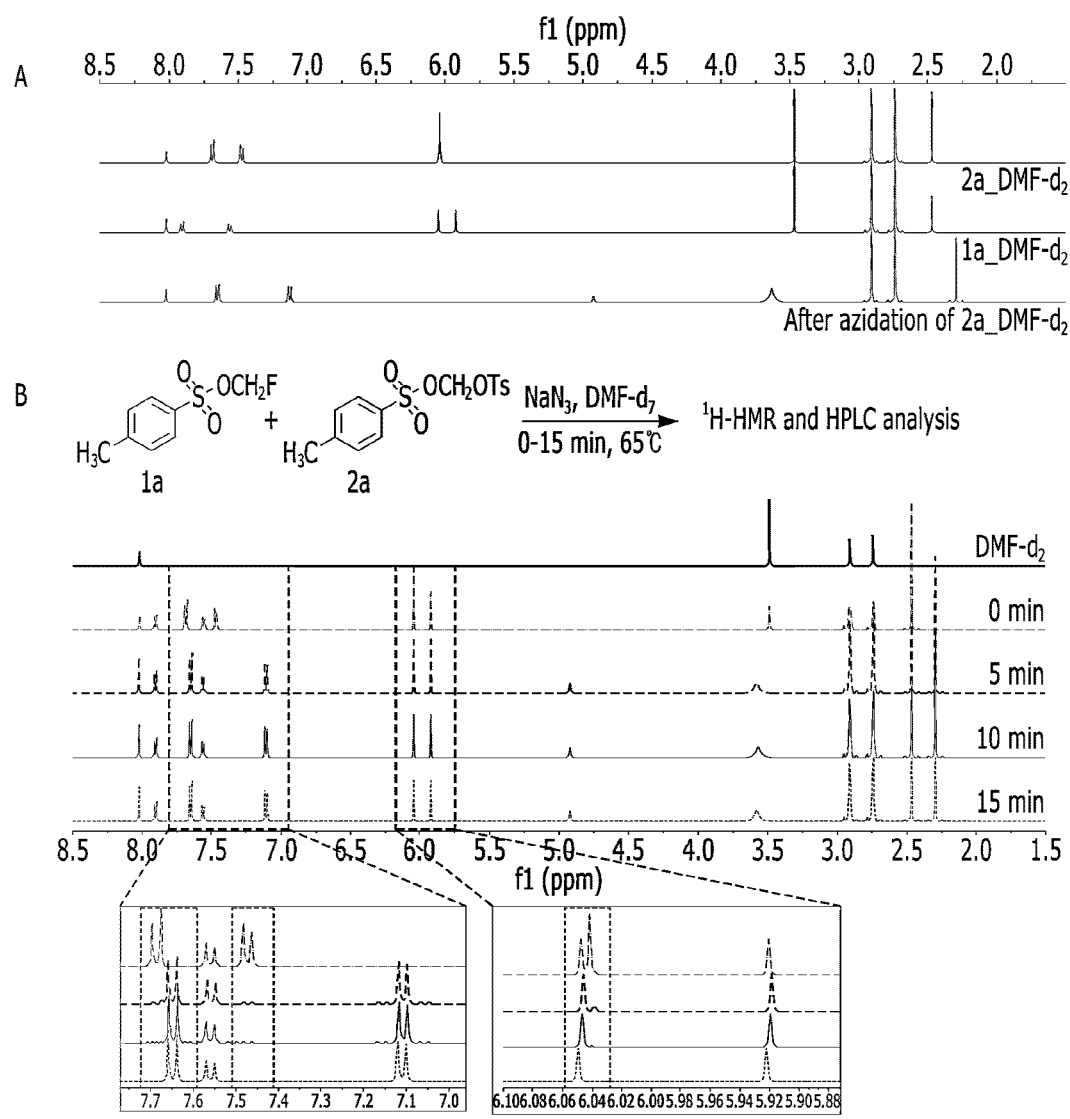
FIG. 3 presents the $^1$H NMR (Nuclear Magnetic Resonance, DMF-d$_7$) spectrums: (A) is for the crude mixture of an azide substitution reaction using same equivalents of fluoromethyltosylate 1a and bis(tosyloxy)methane 2a, prior to the azide substitution reaction according to the embodiment of the present invention; and (B) is for the crude mixture of an azide substitution reaction using same equivalents of fluoromethyltosylate 1a and bis(tosyloxy)methane 2a, after the azide substitution reaction performed in the presence of NaN$_3$ at 65° C. for 0, 5, 10, and 15 minutes.

FIG. 1 illustrates the chemical structures of fluorine-18-labeled fluoromethyl-substituted radiopharmaceuticals that can be produced by the synthesis of a [$^{18}$F]fluoromethyltosylate compound according to the embodiment of the present invention. FIG. 2 illustrates the schemes for a preparation method B for fluorine-18-labeled fluoromethyl-substituted radiopharmaceutical using the synthesis of a [$^{18}$F]fluoromethyltosylate compound via a selective azide substitution reaction and precursor scavenging and a conventional preparation method A for fluorine-18-labeled fluoromethyl-substituted radiopharmaceutical requiring an HPLC separation process. FIG. 3 presents the $^1$H NMR (Nuclear Magnetic Resonance, DMF-d$_7$) spectrums: (A) is for the crude mixture of an azide substitution reaction using same equivalents of fluoromethyltosylate 1a and bis(tosyloxy)methane 2a, prior to the azide substitution reaction according to the embodiment of the present invention; and (B) is for the crude mixture of an azide substitution reaction using same equivalents of fluoromethyltosylate 1a and bis (tosyloxy)methane 2a, after the azide substitution reaction performed in the presence of NaN$_3$ at 65° C. for 0, 5, 10, and 15 minutes.

Figure 4:
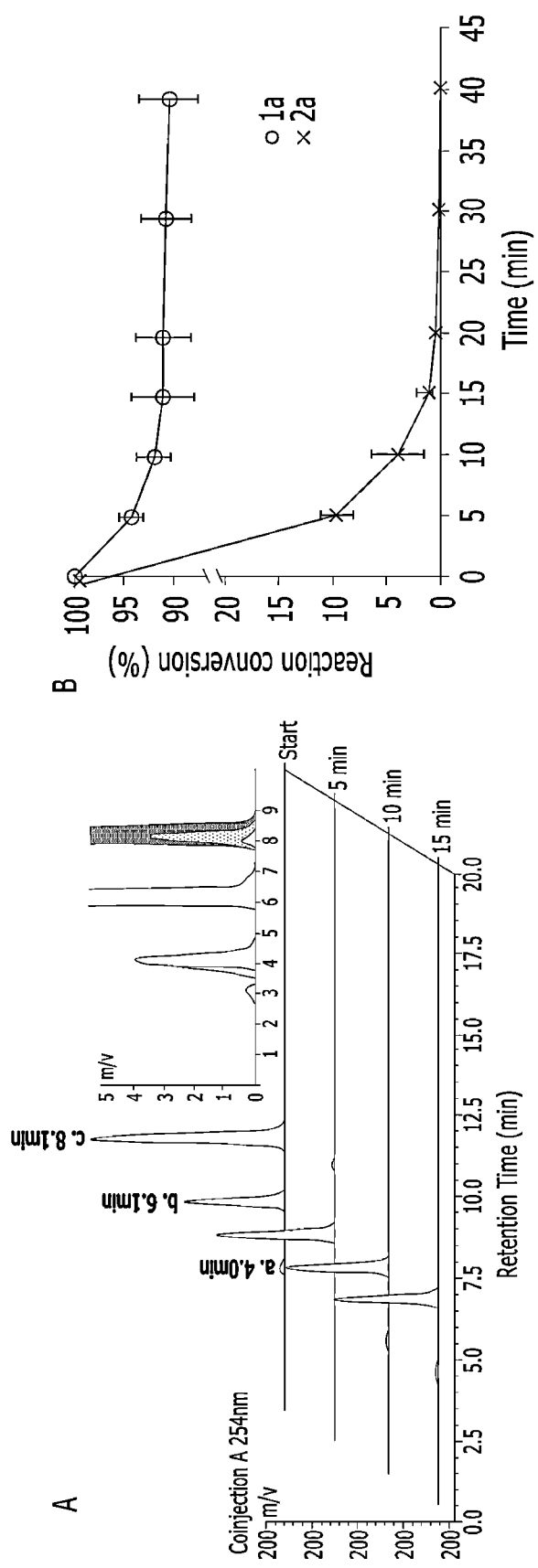
FIG. 4 presents the chromatograms generated from the HPLC of a compound obtained by an azide substitution reaction performed in the presence of NaN$_3$ at 65° C. for 0, 5, 10, and 15 minutes in the same manner as in FIG. 3 according to the embodiment of the present invention: (A) shows three prominent peaks under the HPLC conditions (Xterra RP-C18; 70-30% acetonitrile-water; flow rate 3 mL/min) ((a) system peak, T$_R$=4.0 min; (b) peak for 1a, T$_R$=6.1 min; (c) peak for 2a, T$_R$=8.1 min); and (B) shows the conversion rate of same equivalents of reactants 1 and 2a in percentage as a function of time during the azide substitution reaction.
Figure 5:
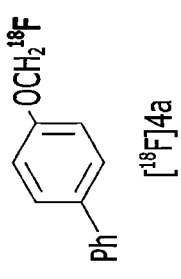
FIG. 5 presents the chromatograms generated from a radio-TLC scanner for the synthesis results acquired in the method for preparing an [$^{18}$F]fluoromethyl-substituted radiopharmaceutical using a selective azide substitution reaction according to the embodiment of the present invention: (A) is for the synthesis results of 4-phenylphenol ([$^{18}$F]4a) obtained by an alkylation reaction of [$^{18}$F]fluoromethyltosylate ([$^{18}$F]1a) and 4-phenylphenol, where the [$^{18}$F]fluoromethyltosylate ([$^{18}$F]1a) is obtained by performing a fluorine-18 labeling reaction of bis(tosyloxy)methane 2a; and (B) is for the synthesis results of 4-phenylphenol ([$^{18}$F]4a) obtained by an alkylation reaction of 4-phenylphenol after performing a selective azide substitution reaction on a crude mixture containing [$^{18}$F]fluoromethyltosylate ([$^{18}$F]1a) obtained by a fluorine-18 labeling reaction.
Figure 5:
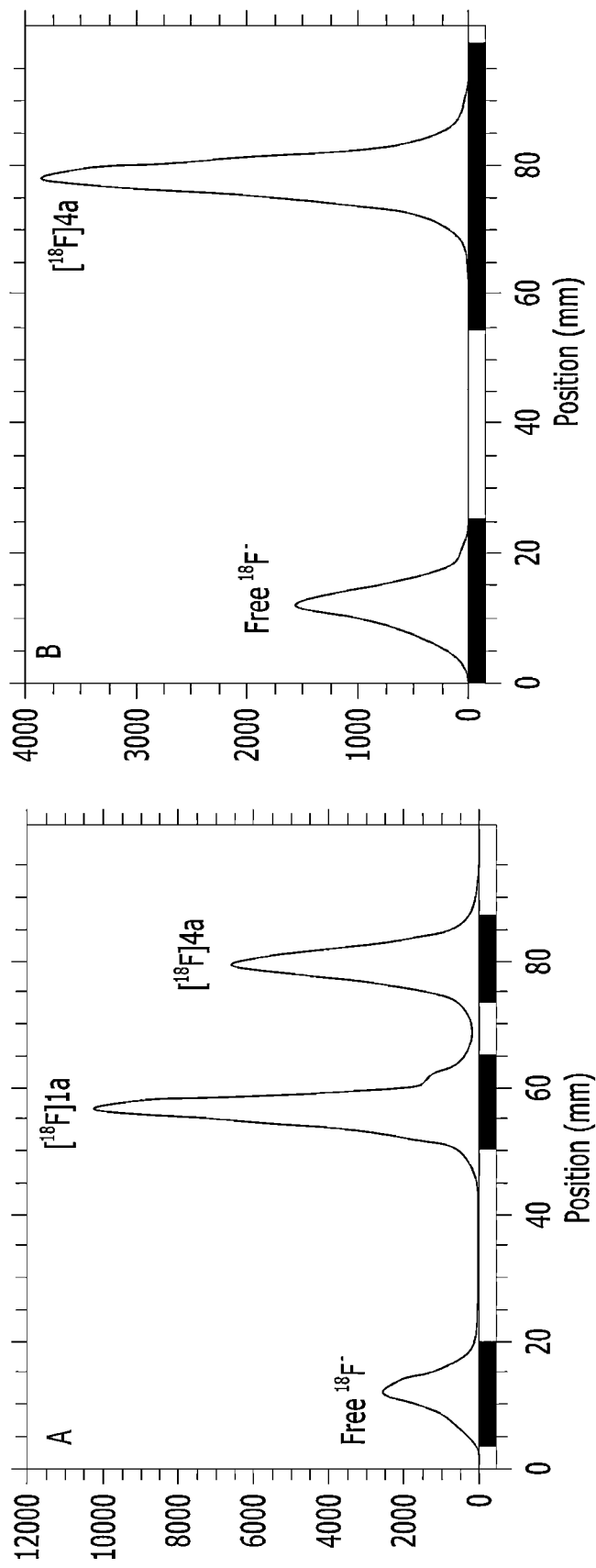
Figure 6:
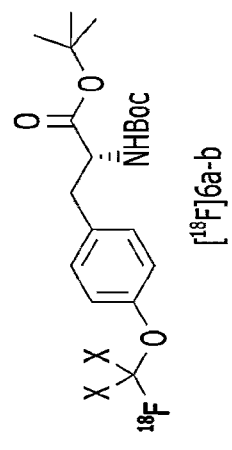
FIG. 6 presents chromatograms generated from a radio-TLC scanner for [$^{18}$F]6a obtained by performing an azide substitution reaction and a precursor scavenging reaction according to the method for preparing a fluorine-18-labeled fluoromethyl-substituted radiopharmaceutical using a selective azide substitution reaction and precursor scavenging according to the present invention.
Figure 6:
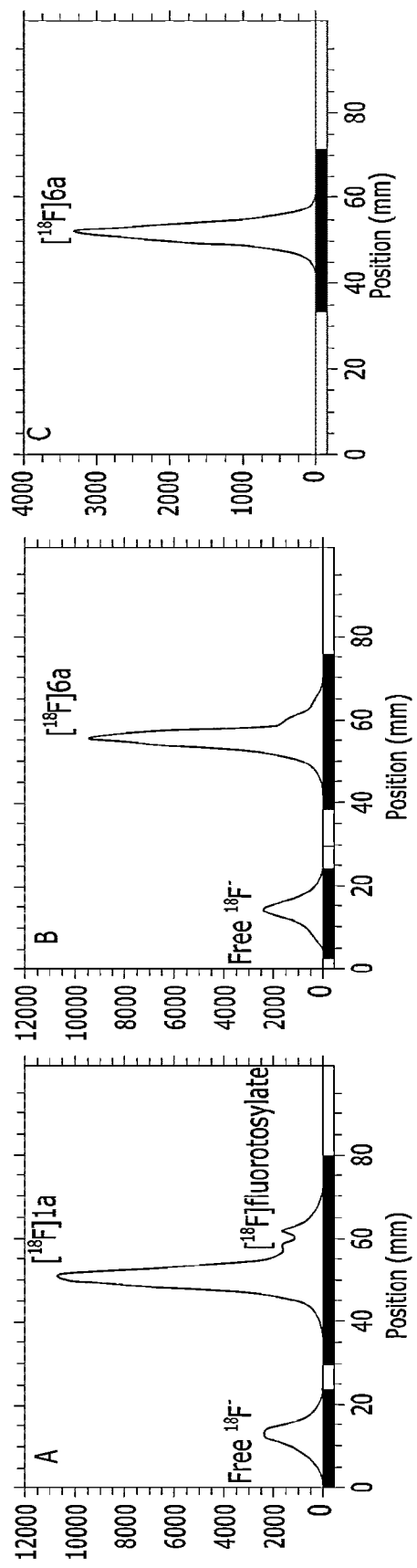

FIG. 4 presents the chromatograms generated from the HPLC of a compound obtained by an azide substitution reaction performed in the presence of NaN$_3$ at 65° C. for 0, 5, 10, and 15 minutes in the same manner as in FIG. 3 according to the embodiment of the present invention: (A) shows three prominent peaks under the HPLC conditions (Xterra RP-C18; 70-30% acetonitrile-water; flow rate 3 mL/min) ((a) system peak, $T_R$=4.0 min; (b) peak for 1a, $T_R$=6.1 min; (c) peak for 2a, $T_R$=8.1 min); and (B) shows the conversion rate of same equivalents of reactants 1 and 2a in percentage as a function of time during the azide substitution reaction. FIG. 5 presents the chromatograms generated from a radio-TLC scanner for the synthesis results acquired in the method for preparing an [$^{18}$F]fluoromethyl-substituted radiopharmaceutical using a selective azide substitution reaction according to the embodiment of the present invention: (A) is for the synthesis results of 4-phenylphenol ([$^{18}$F]4a) obtained by an alkylation reaction of [$^{18}$F]fluoromethyltosylate ([$^{18}$F]1a) and 4-phenylphenol, where [$^{18}$F]fluoromethyltosylate ([$^{18}$F]1a) is obtained by performing a fluorine-18 labeling reaction of bis(tosyloxy)methane 2a; and (B) is for the synthesis results of 4-phenylphenol ([$^{18}$F]4a) obtained by an alkylation reaction of 4-phenylphenol after performing a selective azide substitution reaction on a crude mixture containing [$^{18}$F]fluoromethyltosylate ([$^{18}$F]1a) obtained by a fluorine-18 labeling reaction. FIG. 6 presents chromatograms generated from a radio-TLC scanner for [$^{18}$F]6a obtained by performing an azide substitution reaction and a precursor scavenging reaction according to the method for preparing a fluorine-18-labeled fluoromethyl-substituted radiopharmaceutical using a selective azide substitution reaction and precursor scavenging according to the present invention.

Figure 7:
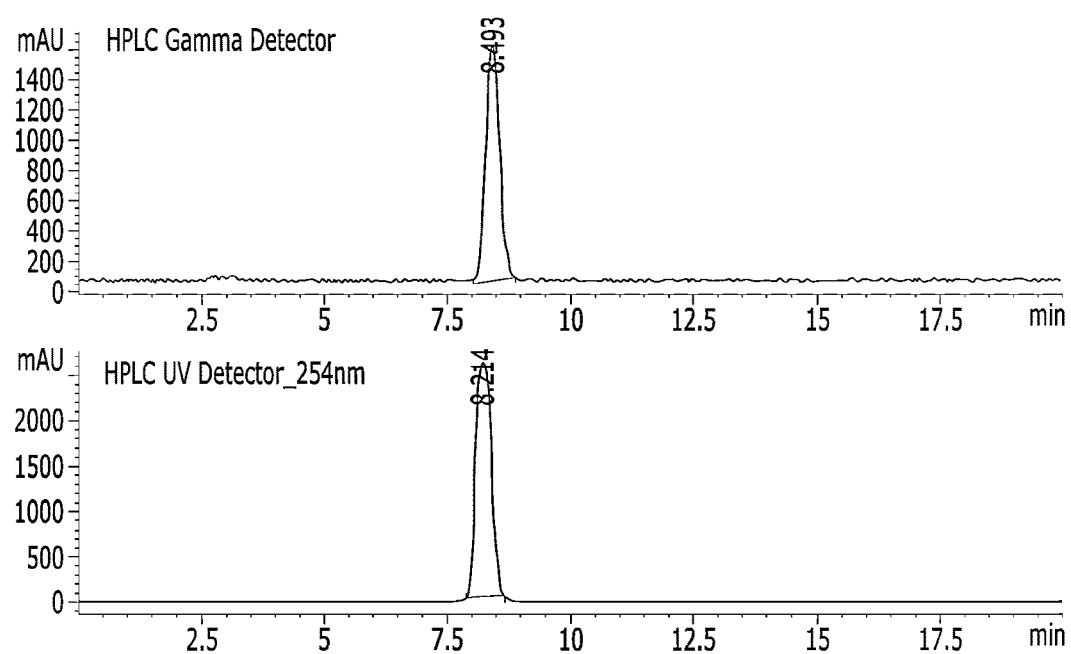
FIG. 7 presents chromatograms generated from the HPLC of a radioligand into which [$^{18}$F]1a and 1a are incorporated at the same time in the method for preparing a fluorine-18-labeled fluoromethyl-substituted radiopharmaceutical using a selective azide substitution reaction and precursor scavenging according to the present invention.
Figure 8:
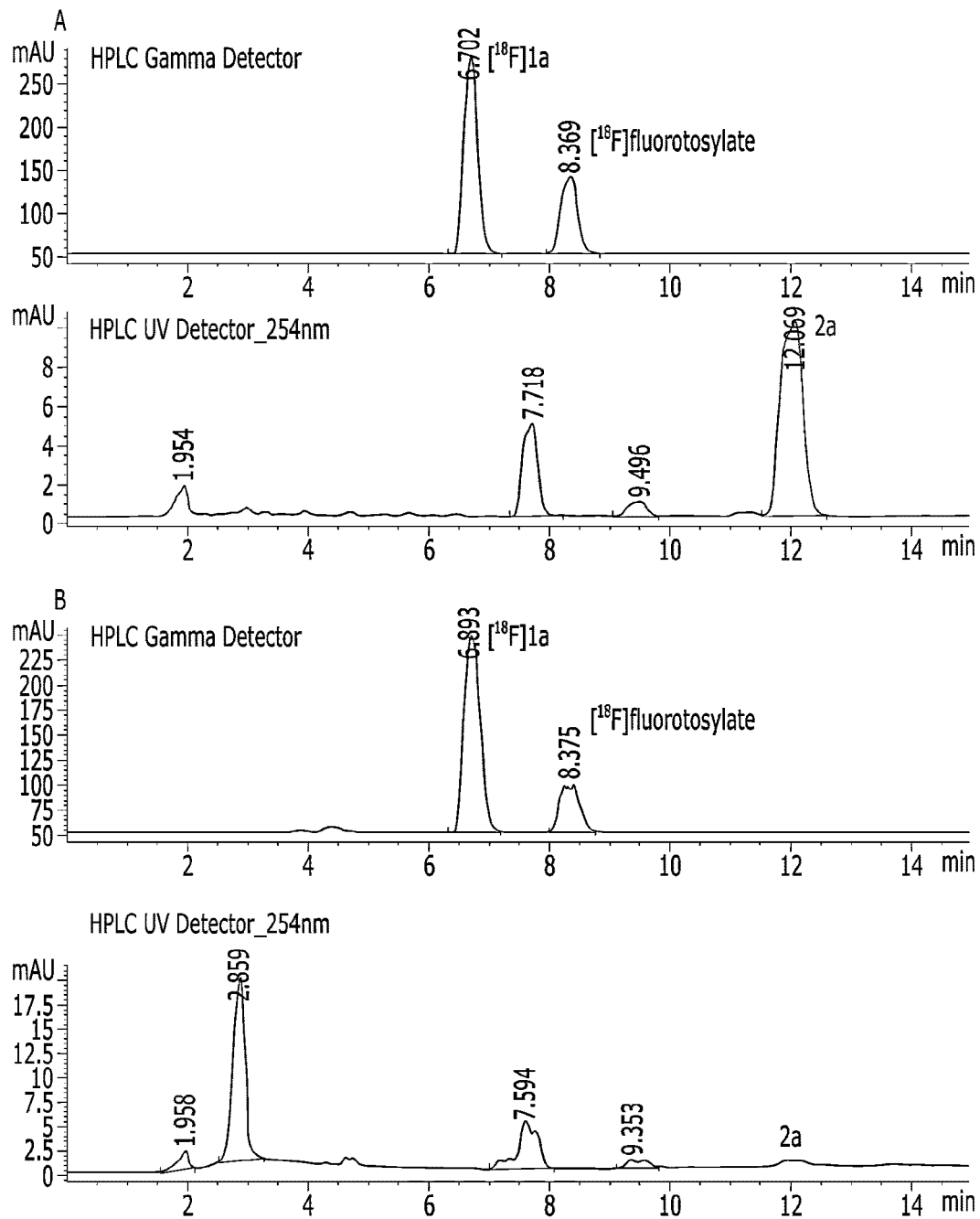
FIG. 8 presents chromatograms generated from the HPLC of a crude mixture A of [$^{18}$F]1a before an azide substitution reaction and a crude mixture B of [$^{18}$F]1a after an azide substitution reaction in the method for preparing a fluorine-18-labeled fluoromethyl-substituted radiopharmaceutical using a selective azide substitution reaction and precursor scavenging according to the present invention.
Figure 9:
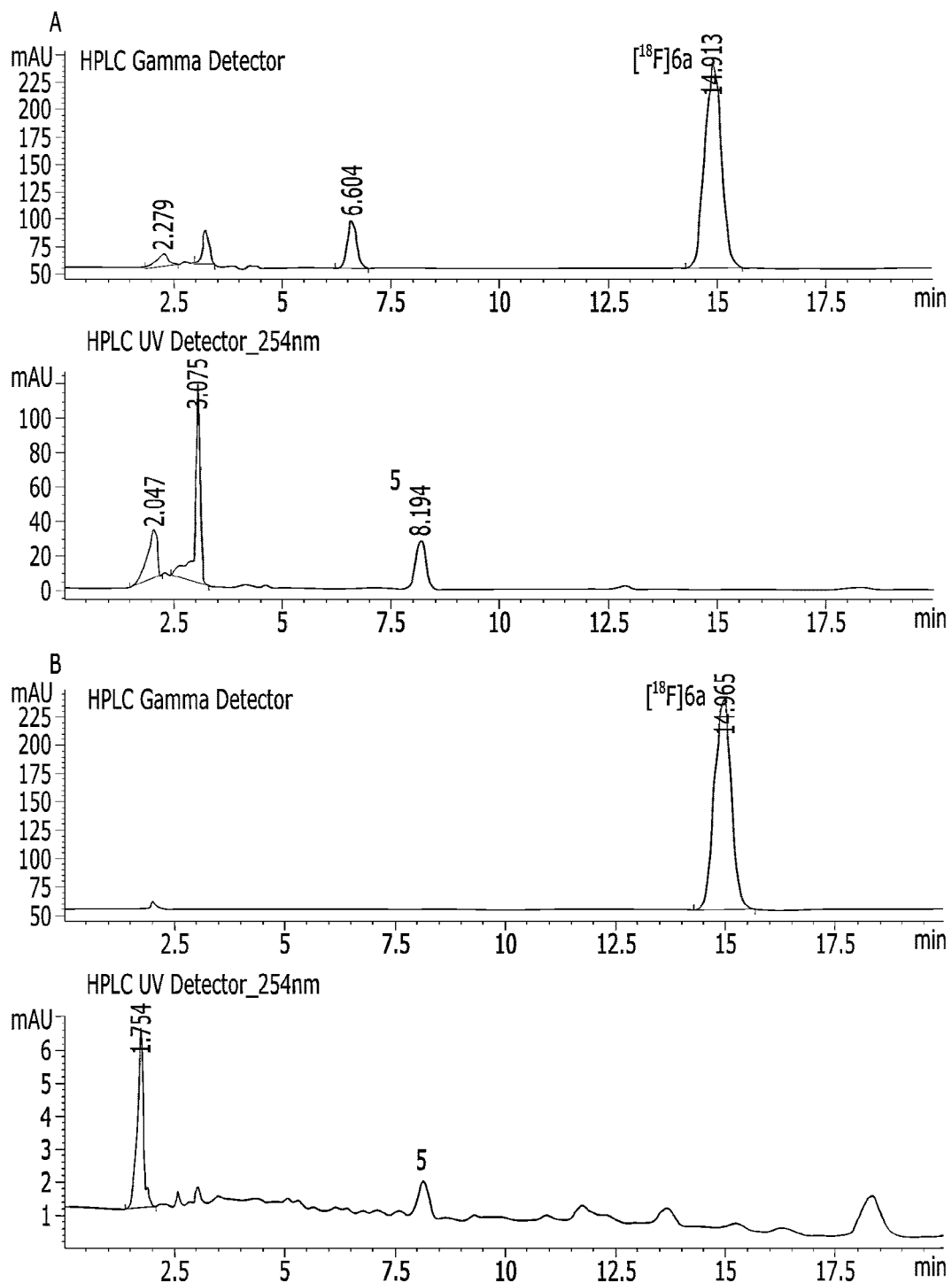
FIG. 9 presents chromatograms generated from the HPLC of a crude mixture A of [$^{18}$F]6a before the addition of a precursor scavenger and a crude mixture B of [$^{18}$F]1a after the addition of a precursor scavenger in the method for preparing a fluorine-18-labeled fluoromethyl-substituted radiopharmaceutical using a selective azide substitution reaction and precursor scavenging according to the present invention.

FIG. 7 presents chromatograms generated from the HPLC of a radioligand into which [$^{18}$F]1a and 1a are incorporated at the same time in the method for preparing a fluorine-18-labeled fluoromethyl-substituted radiopharmaceutical using a selective azide substitution reaction and precursor scavenging according to the present invention. FIG. 8 presents chromatograms generated from the HPLC of a crude mixture A of [$^{18}$F]1a before an azide substitution reaction and a crude mixture B of [$^{18}$F]1a after an azide substitution reaction in the method for preparing a fluorine-18-labeled fluoromethyl-substituted radiopharmaceutical using a selective azide substitution reaction and precursor scavenging according to the present invention. FIG. 9 presents chromatograms generated from the HPLC of a crude mixture A of [$^{18}$F]6a before the addition of a precursor scavenger and a crude mixture B of [$^{18}$F]1a after the addition of a precursor scavenger in the method for preparing a fluorine-18-labeled fluoromethyl-substituted radiopharmaceutical using a selective azide substitution reaction and precursor scavenging according to the present invention.

Referring to these drawings, the method for preparing a fluorine-18-labeled fluoromethyl-substituted radiopharmaceutical using a selective azide substitution reaction according to the present invention comprises: (1) obtaining a [$^{18}$F]fluoride from a cyclotron through an $^{18}$O (p,n)$^{18}$F reaction; (2) separating the [$^{18}$F] fluoride using an acetonitrile reaction solution containing dissolved K$_{2,2,2}$ and K$_2$CO$_3$ to obtain a [$^{18}$F]F$^-$/H$_2$$^{18}$O solution; (3) heating the [$^{18}$F]F$^-$/H$_2$$^{18}$O solution to obtain K$_{2,2,2}$/K$^{18}$F; (4) placing the K$_{2,2,2}$/K$^{18}$F along with a bis(tosyloxy)methane compound (2a-b) into a reactor and adding a reaction solution to cause a reaction and obtain a first precursor solution; (5) cooling the first precursor solution and adding an azide compound to cause an azide substitution reaction selectively on the bis (tosyloxy)methane compound present in the first precursor solution and obtain a [$^{18}$F]fluoromethyltosylate compound; (6) adding a bioactive molecule to the [$^{18}$F]fluoromethyltosylate compound to cause an alkylation reaction and obtain a second precursor solution; and (7) adding a precursor scavenger to the second precursor solution and scavenging unreacted precursors to produce a fluorine-18-labeled fluoromethyl-substituted radiopharmaceutical without a separate HPLC separation process.

That is, the method for preparing a fluorine-18-labeled fluoromethyl-substituted radiopharmaceutical using a selective azide substitution reaction and precursor scavenging according to the present invention involves performing a selective azide substitution on the excess bis(tosyloxy)methane compound present in the crude mixture in the first process of synthesizing a fluorine-18-labeled fluoromethyl-substituted radiopharmaceutical to impose inactivity in the second process of fluoromethyl substitution and also using a scavenger to cause a selective reaction on the excess crude mixture during the substitution reaction, so it can not only synthesize a radiopharmaceutical with improved radiochemical yield and high radiochemical purity while avoiding an HPLC separation/purification process necessary to the synthesis of fluorine-18-labeled fluoromethyl-substituted radiopharmaceuticals, but reduce the manufacturing time and cost. Here, the bis(tosyloxy)methane compound may be a compound having a structure of the following chemical formula 1.

[Chemical Formula 1]

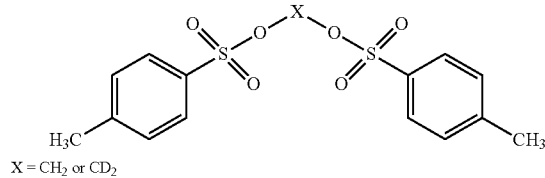

X = CH$_2$ or CD$_2$

In addition, the [$^{18}$F]fluoromethyltosylate compound may include [$^{18}$F]fluoromethyltosylate or deuterium-substituted [$^{18}$F]fluoromethyltosylate as given by the following chemical formula 2.

[Chemical Formula 2]

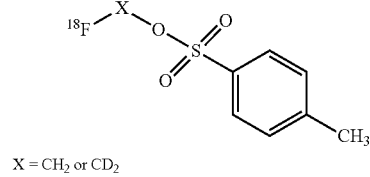

X = CH$_2$ or CD$_2$

The step (2) of obtaining the [$^{18}$F]F$^-$/H$_2$$^{18}$O solution may be performed by separating the [$^{18}$F] fluoride using an acetonitrile reaction solution containing dissolved K$_{2,2,2}$ and K$_2$CO$_3$ on a Chromafix-HCO$_3$ cartridge or a quaternary methyl ammonium (QMA) anion exchange cartridge.

The step (3) of obtaining the K$_{2,2,2}$/K$^{18}$F is preferably performed by completely removing water from the [$^{18}$F]F$^-$/H$_2$$^{18}$O solution at temperatures of 50 to 180° C. in the nitrogen gas atmosphere.

The step (4) of obtaining the first precursor solution is preferably performed by placing the K$_{2,2,2}$/K$^{18}$F along with a bis(tosyloxy)methane compound into a reactor and adding an acetonitrile reaction solution to cause a reaction at 80 to 180° C. for 1 to 30 minutes. Here, the bis(tosyloxy)methane compound may be bis(tosyloxy)methane or deuterium-substituted bis(tosyloxy)methane-d$_2$ as given by the chemical formula 1.

The azide substitution reaction of the step (5) may be performed at 40 to 100° C. for 2 to 10 minutes by adding an azide compound, such as tetrabutyl azide (nBu$_n$NH$_3$), to the first precursor solution.

The step (6) of obtaining the second precursor solution may be performed by the alkylation reaction, such as an O-, N-, S-, P-alkylation reaction given by the following chemical formula 3.

[Chemical Formula 3]

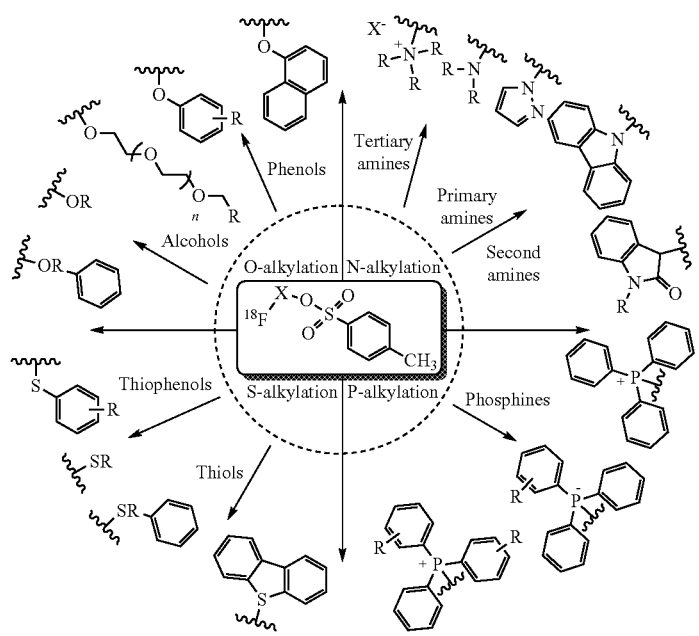

R=aromatic or aliphatic functional group

X=hydrogen or deuterium-substituted methyl group

The precursor scavenger may be a scavenger selected from the group consisting of guanidine-based heterocycles and isocyanates (e.g., MTBD (7-methyl-1,5,7-triazacyclo [4.4.0]dec-5-ene, resin bound isocyanate, or benzyl isocyanate).

On the other hand, the method may further include performing a cartridge separation of the fluorine-18-labeled fluoromethyl-substituted radiopharmaceutical on a cartridge packed with silica or C18-substituted silica to increase the purity of the fluorine-18-labeled fluoromethyl-substituted radiopharmaceutical. The solvent as used in the cartridge separation step may be acetonitrile or a mixed solution, such as acetonitrile-water mixture, ethylacetate-hexane mixture, acetonitrile-hexane mixture, methanol-hexane mixture, or ethanol-hexane mixture.

The preparation method may be performed on an automated synthesis device and a cassette system. The automated synthesis device includes, for example, TRACERLab FX-FN or GE TRACERLab FX N Pro, commercially available from GE Health healthcare. The cassette system includes, for example, AllinOne commercialized by Trasis, Explore™ One by Simens, or FASTlab™ series by GE Health healthcare.

Example 1

Hereinafter, reference will be made to examples to give a detailed description as to the experimental procedures using F-19 and F-18 produced by the method for preparing a fluoromethyl-substituted radiopharmaceutical using a selective azide substitution reaction and precursor scavenging according to the present invention.

<Experimental Example 1>

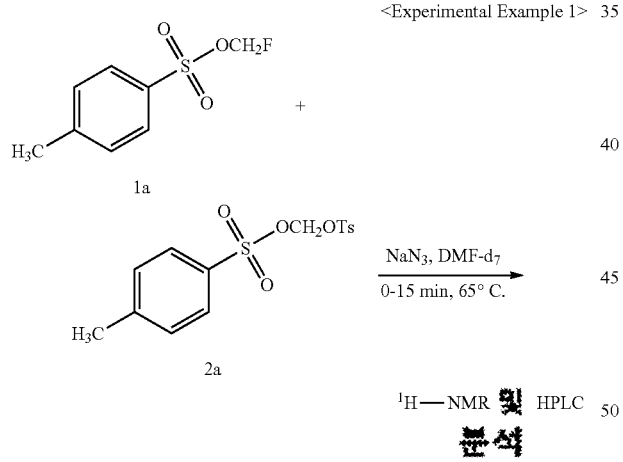

Same equivalents (4.9 mmol) of 1a and 2a were dissolved in an NMR solvent, DMF-d$_7$, and NaN$_3$ (2.5 equivalent, 12.3 mmol) was then added to cause a reaction at 65° C. The results of the reaction were analyzed using NMR and HPLC every 5, 10 or 15 minutes, depending on time, in comparison to the results at 0 minute when the azide compound was not yet added. It was predicted that the azide anion (N$_3^-$) would react competitively with 1a and 2a and cause an azide substitution reaction preferentially on the bis(tosyloxy) methane which was richer in electrons in the carbon of the methyl group. As predicted, the bis(tosyloxy)methane was exceptionally more reactive to the azide compound than the fluoromethyltosylate. The results of the selective reaction of the azide on the compound having two tosyl groups and the compound having a single tosyl group were summarized in FIG. 3. It was confirmed that 1a became very stable in 5 minutes, while the azide was very rapidly incorporated into 2a to convert 2a into diazidomethane. According to the NMR results, 2a was completely converted into diazidomethane in 15 minutes. This showed that NaN$_3$ acted as a very strong and selective nucleophile, but there was found no azidomethyltosylate as a by-product possibly created as an intermediate of the diazidomethane synthesis. The HPLC results were analyzed using calibration curves of 1a and 2a. As shown in FIG. 4A, the first one (T$_R$=4.0 min) of the three peaks was a system peak, and the second one (T$_R$=6.1 min) and the third one (T$_R$=8.1 min) represented 1a and 2a, respectively. Likewise, the azide substitution reaction of 2a took place in an exceptionally short time and, relatively, that of 1a rarely proceeded. In 10 minutes, when calculated by the UV value, 94% of 1a remained stable and 96.1% of 2a was converted into diazidomethane. In 40 minutes, 90% of 1a remained stable and at least 99.9% of 2a disappeared.

<Experimental Example 2>

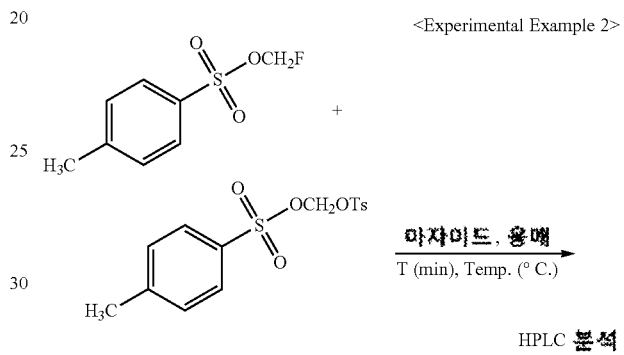

TABLE 1

Selective Azide Substitution Reaction Using Different Azide Compounds (n > 3)

| No. | Base | Solvent | 2a[a] yield | 1a[a] stability |
|---|---|---|---|---|
| 1 | NaN$_3$ | DMF | 96.1 ± 2.4 | 91.9 ± 1.7 |
| 2 | LiN$_3$ | DMF | 91.0 ± 3.8 | 94.7 ± 1.2 |
| 3 | KN$_3$ | DMF | >99.5 | 91.0 ± 4.5 |
| 4 | KN$_3$ | DMA | >99.5 | 62.0 ± 3.9 |
| 5 | nBu$_4$NN$_3$ | DMF | 98.6 ± 1.3 | 93.6 ± 0.9 |
| 6 | nBu$_4$NN$_3$ | DMA | 98.9 ± 0.9 | 93.4 ± 2.0 |
| 7 | nBu$_4$NN$_3$ | DMA | >99.5 | 94.0 ± 4.2 |
| 8 | nBu$_4$NN$_3$ | DMSO | 91.0 ± 2.1 | 89.9 ± 3.3 |
| 9 | nBu$_4$NN$_3$ | CH$_3$CN | 84.2 ± 4.5 | 98.6 ± 1.3 |
|   |   |   | (86.0 ± 3.6)[b] | (98.8 ± 1.6)[b] |
| 10 | nBu$_4$NN$_3$ | CH$_3$CN | >99.5 | 96.3 ± 3.1 |
| 11 | nBu$_4$NN$_3$ | THF | >99.5 | 86.2 ± 1.7 |
| 12 | nBu$_4$NN$_3$ | Benzene | >99.5 | 87.6 ± 2.0 |
| 13 | nBu$_4$NN$_3$ | 1,4-dioxane | 93.1 ± 3.2 | 98.1 ± 1.6 |
| 14 | nBu$_4$NN$_3$ | t-BuOH | 43.2 ± 5.6 | 97.1 ± 2.3 |
| 15 | nBu$_4$NN$_3$ | MeOH | 53.9 ± 2.0 | 90.1 ± 1.2 |

[a]2a yield and 1a stability were analyzed by HPLC after reaction.
[b]Results of deuterium-substituted compound This experiment was performed in order to determine the effects of the type of the azide reagent, the solvent and the temperature on the selective azide substitution reaction. The reaction results were summarized in Table 1. Same equivalents (4.9 mmol) of 1a and 2a along with different azide reagents (12.3 mmol) were dissolved in DMF, and a reaction was preceded at 65° C. for 10 minutes to determine the tendency of the compounds to change. In item numbers 1, 2, 3, and 5 of the table, KN$_3$ caused the greatest change from 2a to 3a, while 1a had high stability. 1b in which a deuterium-substituted reaction solvent was used had a slightly lower stability than 1a. When the amount of the azide reagent was doubled, it did not affect the stability of 1a (in item number 7), but at high temperatures, the stability of 1a was affected (in item number 4). nBu$_4$NN$_3$ was used because it was more soluble in most of solvents than other azide reagents. In this case, 1a showed a higher stability in DMA and DMF, but 2a was not completely converted into 3a. In order to overcome this issue, the amount of nBu$_4$NN$_3$ was increased six times (in item number 10). nBu$_4$NN$_3$ exhibited high selectivity even in non-polar solvents such as benzene or 1,4-dioxane (in item numbers 12 and 13). Yet, the stability of 1a was more reduced in benzene. The ability for the azide substitution reaction deteriorated in t-butanol and methanol (in item numbers 14 and 15).

Experimental Example 3

TABLE 2

Results[a] of 18-fluorine labeling Using Selective Azide Substitution Reaction

| | Results |
|---|---|
| RCC (%)[b] | 94.5 ± 1.6 (96.9 ± 2.5)[c] |
| RCY (%)[d] | 70.3 ± 6.4 (72.1 ± 4.2)[c] |
| Unreacted 2a-b | 1.3 ± 0.3 µmol (1.4 ± 0.3 µmol)[c] |
| [$^{18}$F]1a-b stability (%) | 99.4 ± 0.5 (99.6 ± 0.3)[c] |
| 2a-b (%) remaining after selective azidation | Not detected (Not detected)[c] |

[a]Selective azidation (in situ reaction) was performed after fluorine labeling reaction.
[b]Measured by RCC (radiochemical conversion), RCY (radiochemical yield), radio-TLC.
[c]Results of deuterium-substituted compound.
[d]Measured after HPLC separation.

The reaction for synthesis of a [$^{18}$F]fluoromethyltosylate compound ([$^{18}$F]1a-b) from the bis(tosyloxy)methane compound (2a-b) was performed under the general labeling conditions of the above-specified aliphatic nucleophile substitution reaction. The radiochemical conversion yields of the [$^{18}$F]fluoromethyltosylate compound ([$^{18}$F]1a-b) measured with a radio-TLC scanner were respectively 94.5±1.6% and 96.9±2.5% (Refer to Table 2), and the radiochemical yields measured after HPLC separation were 70.3±6.4% ([$^{18}$F]1a) and 72.1±4.2% ([$^{18}$F]1b). The amount of the excess bis(tosyloxy)methane compound (2a-b) remaining unreacted prior to the azide substitution reaction was 1.3±0.3 µmol and 1.4±0.3 µmol as determined from the calibration curves. As for the optimized conditions of the azide substitution reaction, nBu$_4$NN$_3$ (24 mg, 84.4 µmol) was added in the acetonitrile solvent and then a reaction was caused at 80° C. for 5 minutes. As a result, it was confirmed by the HPLC system that all the excess 2a-b disappeared, while at least 99% of [$^{18}$F]1a-b having a single tosyl group remained stable relatively.

Experimental Example 4

Comparison of Direct O-Alkylation Method (Route A) and Selective Azide Substitution Reaction (Route B)

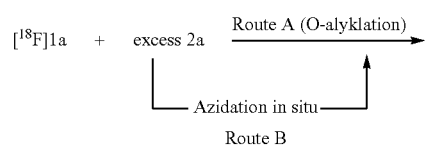

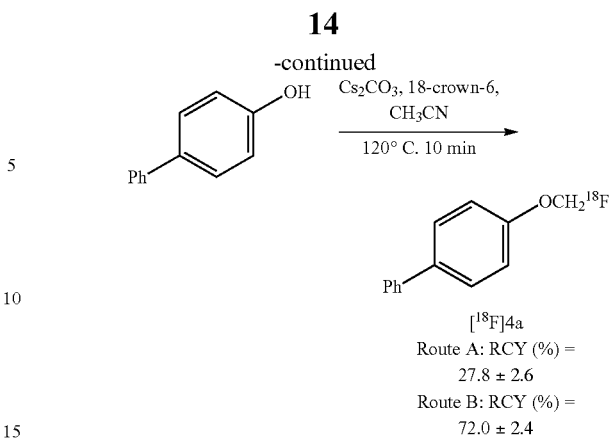

[$^{18}$F]4a
Route A: RCY (%) = 27.8 ± 2.6
Route B: RCY (%) = 72.0 ± 2.4

In order to compare the preparation method for fluoromethyl-substituted radiopharmaceutical under the conditions using an azide substitution reaction and the preparation method without using an azide substitution reaction, an O-alkylation reaction using 4-phenylphenol as a precursor was performed to obtain the results as follows (Scheme 2). Under the conditions using the azide substitution reaction (Route B), the final compound had a high radiochemical yield (72.0%, half-life taken into consideration). On the contrary, when the azide substitution reaction was carried out and relatively excess precursors remained unreacted (Route A), the final compound had an exceptionally low radiochemical yield (27.8%, half-life taken into consideration). Generally, an HPLC separation and purification process is necessary in the case of not using the azide substitution reaction. Yet, if the azide substitution reaction is employed, the final product can be separated to have a sufficiently high purity just by using a cartridge packed with C-18-substituted silica. The results of HPLC analysis confirmed that a by-product ([1,1'-biphenyl]-4-yloxy)methyl 4-methylbenzenesulfonate) not observed in the azide substitution reaction was produced.

Experimental Example 5

Synthesis of [$^{18}$F]Fluoromethyl Tyrosine Using the Present Invention (Selective Azidation & Precursor Scavenging with MTBD Scavenger)

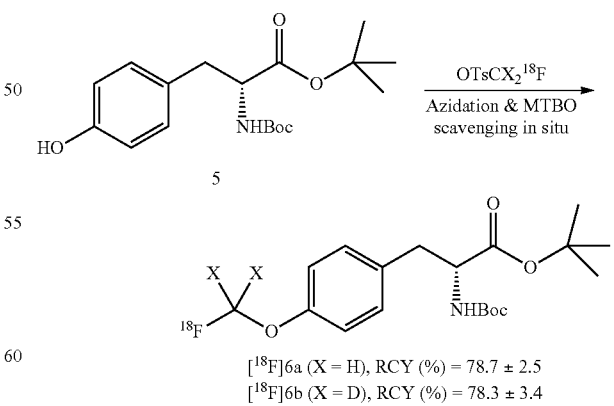

[$^{18}$F]6a (X = H), RCY (%) = 78.7 ± 2.5
[$^{18}$F]6b (X = D), RCY (%) = 78.3 ± 3.4

Here are the results of applying a method of using an azide substitution reaction and precursor scavenging to the synthesis of [$^{18}$F]fluoromethyl tyrosine. The azide substitution reaction was used to synthesize [$^{18}$F]fluoromethyltosylate ([$^{18}$F]1a-b), at least 99.5% of which participated in an O-alkylation reaction. After a labeling reaction, a precursor was added to the crude mixture, and the excess precursor remaining was caused to participate in the reaction at the room temperature and create an ion form. The amount of the precursor remaining after the reaction was 1.8% or less. The final target compound, [$^{18}$F]6a-b was neatly separated just using a cartridge packed with silica or C18-substituted silica, and its radiochemical yields were 78.7% and 78.3%.

<Preparation Example 1> Preparation of Bis(tosyloxy)methane Compound

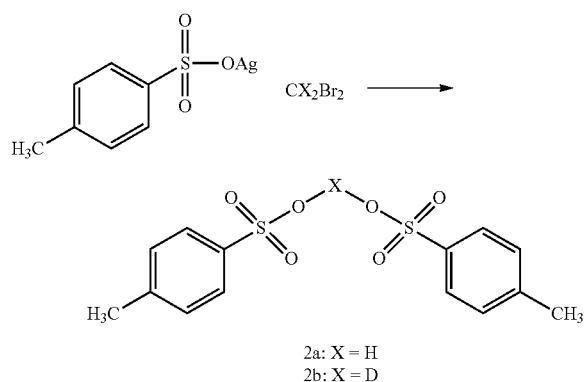

Dibromomethane (500 μL, 7.12 mmol) and silver p-tolusulfonate (4.17 g, 14.95 mmol) were dissolved in acetonitrile (8 mL), following by refluxing for 16 hours. After completion of the reaction, extraction with water and dichloromethane was carried out. The organic solvent layer was isolated, removed of water with sodium sulfate, and filtered out. The filtrate was removed of the solvent to obtain 2a-b as a whitish solid.

Anal. Calculated for ($C_{15}H_{16}O_6S_2$, 2a): C, 50.55; H, 4.53; O, 26.93; S, 17.99%. MS (ESI) m/z 357.24 (M+H$^+$); m.p. 119.9-122.1° C. $^1$H NMR (400 MHz, CDCl$_3$) δ 7.59 (d, J=8.4 Hz, 3H), 7.24 (d, J=8.4 Hz, 4H), 5.81 (s, 2H), 2.45 (s, 6H); $^{13}$C NMR (100 MHz, CDCl$_3$) δ 145.2, 133.1, 129.6, 127.8, 87.79, 21.6.

Anal. Calculated for ($C_{15}H_{14}D_2O_6S_2$, 2b): C, 50.27; H, 5.06; O, 26.78; S, 17.89%. MS (ESI) m/z 359.24 (M+H)+; m.p. 121.1-122.8° C. $^1$H NMR (400 MHz, CDCl$_3$) δ 7.59 (d, J=8.4 Hz, 4H), 7.24 (d, J=8.4 Hz, 4H), 2.45 (s, 6H); $^{13}$C NMR (100 MHz, CDCl$_3$) δ 145.2, 133.1, 129.57, 127.8, 21.5.

<Preparation Example 2> Preparation of Fluoromethyltosylate Compound

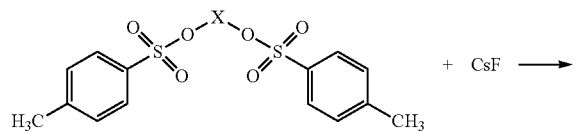

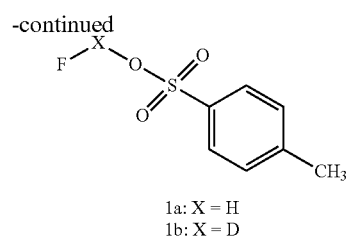

Ditosylate or ditosylate-d$_2$ (40 mmg, 1.12 mmol) was dissolved in acetonitrile (5 mL), and cesium fluoride (256 mg, 1.68 mmol) and hexaethylene glycol (0.45 mL, 1.80 mmol) were added to cause a reaction at 85° C. for 10 hours. After completion of the reaction, extraction with water and dichloromethane was carried out. The organic solvent layer was isolated, removed of water with sodium sulfate, and filtered out. The filtrate was removed of the solvent and subjected to a separation on a flash column to obtain 1a-b as a colorless liquid.

Anal. Calculated for ($C_8H_9FO_3S$, 1a): C, 47.05; H, 4.44; F, 9.30; O, 23.50; S, 15.70%. MS (ESI) m/z 227.3 (M+Na)$^+$; $^1$H NMR (400 MHz, CDCl$_3$) δ 7.59 (d, J=8.4 Hz, 3H), 7.24 (d, J=8.4 Hz, 4H), 5.81 (s, 2H), 2.45 (s, 6H); $^{13}$C NMR (100 MHz, CDCl$_3$) δ 145.2, 133.1, 129.6, 127.8, 87.79, 21.6. CAS Registry No. provided by the author: 114435-86-8.

Anal. Calculated for ($C_8H_7D_2FO_3S$, 1b): C, 46.59; H, 5.37; F, 9.21; O, 23.27; S, 15.55%. MS (ESI) m/z 229.3 (M+Na)$^+$; $^1$H NMR (400 MHz, CDCl$_3$) δ 7.82 (d, J=8.3 Hz, 2H), 7.35 (d, J=8.3 Hz, 2H), 2.45 (s, 3H); $^{13}$C NMR (100 MHz, CDCl$_3$) δ 145.4, 133.7, 129.8, 127.7, 21.5. CAS Registry No. provided by the author: 1180485-67-9.

<Preparation Example 3> Preparation of 1-Phenyl-4-(fluoromethoxy)benzene

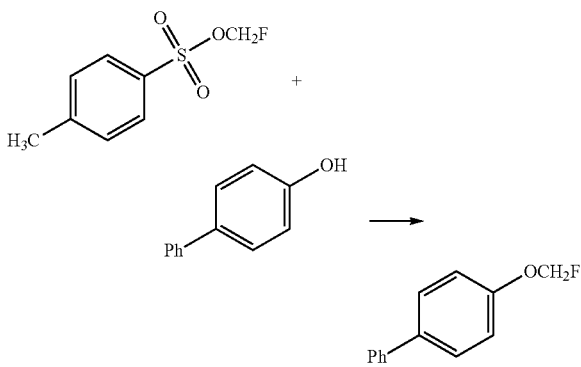

4-phenylphenol (300 mmg, 1.76 mmol) was dissolved in acetonitrile (5 mL), and fluoromethyltosylate (359 mg, 1.76 mmol), cesium carbonate (1.15 g, 3.52 mmol) and 1,4,7,10,13,16-hexaoxacyclooctadecane (1.16 g, 3.52 mmol) were added to cause a reaction at 65° C. for 16 hours. After completion of the reaction, extraction with dichloromethane and water was carried out. The organic solvent layer was isolated, removed of water with sodium sulfate, and filtered out. The filtrate was removed of the solvent and subjected to a separation on a flash column (ethylacetate:hexane=1:4) to obtain a product as a whitish solid.

Anal. Calculated for ($C_{13}H_{11}FO$): C, 77.21; H, 5.48; F, 9.39; O, 7.91%. MS (ESI) m/z 203.1 (M+H)$^+$; m.p. 74.9-

76.3° C.; $^1$H NMR (400 MHz, CDCl$_3$) δ 7.57 (m, 4H), 7.45 (t, J=14.8 Hz, 2H), 7.35 (t, J=14.8 Hz, 2H), 7.17 (m, 2H), 5.76 (d, J=54 Hz, 2H); $^{13}$C NMR (100 MHz, CDCl$_3$) δ 156.1, 140.3, 136.5, 128.6, 128.2, 126.9, 116.8, 100.6 (d, J=218.1 Hz). CAS Registry No. provided by the author: 956707-10-1.

<Preparation Example 4> Preparation of tert-Butyl (R)-2-((tert-butoxycarbonyl)amino)-3-(4-(fluoromethoxy)phenyl)propanoate and tert-butyl (R)-2-((tert-butoxycarbonyl)amino)-3-(4-(fluoromethoxy-d$_2$)phenyl)propanoate (6a-b)

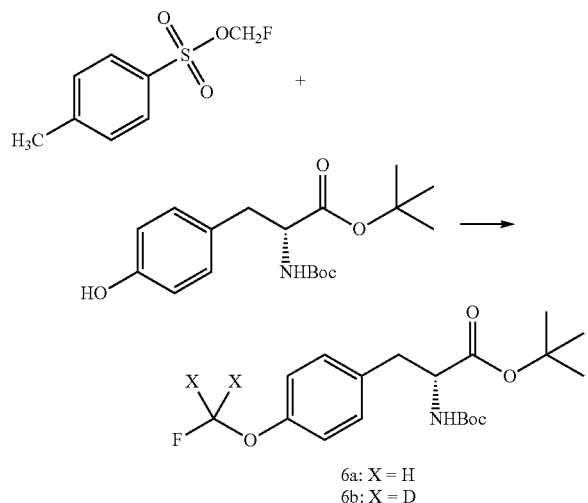

6a: X = H
6b: X = D tert-butyl(tert-butoxycarbonyl)-D-tyrosinate (50 mg, 0.15 mmol) and fluoromethyltosylate or fluoromethyltosylate-d$_2$ (35 mg, 0.17 mmol) were dissolved in dimethylacetamide (1.5 mL), and cesium carbonate (146 mg, 0.45 mmol) and 1,4,7,10,13,16-hexaoxacyclooctadecane (18-crown-6, 158 mg, 0.60 mmol) were added to cause a reaction at 80° C. for one hour. After completion of the reaction, extraction with dichloromethane and water was carried out. The organic solvent layer was isolated, removed of water with sodium sulfate, and filtered out. The filtrate was removed of the solvent and subjected to a separation on a flash column (ethylacetate:hexane=1:4) to obtain a product as a light yellowish liquid.

Anal. Calculated for (C$_{19}$H$_{28}$FNO$_5$, 6a): C, 61.77; H, 7.64; F, 5.14; N, 3.79; O, 21.65. MS (ESI) m/z 370.2 (M+H)$^+$; $^1$H NMR (400 MHz, CDCl$_3$) δ 7.13 (d, J=8.6 Hz, 2H), 7.00 (d, J=8.6 Hz, 2H), 5.69 (d, J=52 Hz, 2H), 5.04-4.90 (m, 1H), 4.50-4.33 (m, 1H), 3.09-2.94 (m, 2H), 1.41 (d, 18H); $^{13}$C NMR (100 MHz, CDCl$_3$) δ170.7, 155.6, 154.9, 131.4, 130.6, 116.4, 100.7 (d, J=218.1 Hz), 81.9, 79.5, 54.7, 37.5, 28.2, 27.8.

Anal. Calculated for (C$_{19}$H$_{26}$D$_2$FNO$_5$, 6b): C, 61.44; H, 8.14; F, 5.11; N, 3.77; O, 21.54. MS (ESI) m/z 372.2 (M+H)$^+$; $^1$H NMR (400 MHz, CDCl$_3$) δ 7.13 (d, J=8.6 Hz, 2H), 7.00 (d, J=8.6 Hz, 2H), CD$_2$ (not observed), 5.04-4.90 (m, 1H), 4.49-4.35 (m, 1H), 3.09-2.94 (m, 2H), 1.42 (d, 18H); $^{13}$C NMR (100 MHz, CDCl$_3$) δ170.7, 155.6, 154.9, 131.4, 130.6, 116.4, CD$_2$ (not observed), 81.9, 79.5, 54.7, 37.5, 28.2, 27.8.

<Preparation Example 5> Synthesis of [$^{18}$F]fluoromethyltosylate Compound ([$^{18}$F] 1a-b)

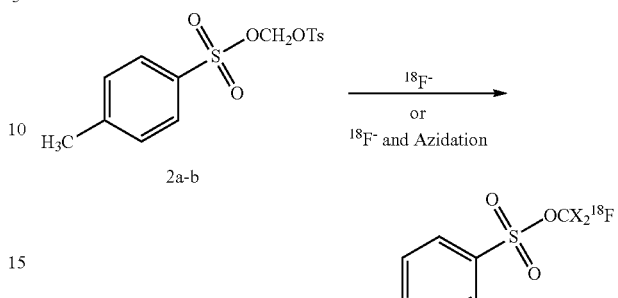

[$^{18}$F]1a-b (X = H or D)

[$^{18}$F]fluoride was produced using an $^{18}$O (p,n)$^{18}$F reaction. [$^{18}$F]F/H$_2$$^{18}$O was separated on a chromafix-HCO$_3$ cartridge using a mixture of acetonitrile and water in which K$_{2.2.2}$ and K$_2$CO$_3$ were dissolved. The separated solution was completely removed of water using nitrogen gas at 50 to 180° C. Bis(tosyloxy)methane or bis(tosyloxy)methane-d$_2$ was added to the water-free K$_{2.2.2}$/K$^{18}$F, and the mixture was placed in a reactor and dissolved in a mixed solvent of acetonitrile and water, followed by a reaction at 80 to 180° C. for 1 to 30 minutes. After completion of the reaction, a radio-TLC scanner was used to determine the radiochemical conversion yield. The amount of the excess bis(tosyloxy)methane compound remaining unreacted was determined by HPLC separation.

<Preparation Example 6> Preparation of 1-Phenyl-4-([$^{18}$F]fluoromethoxy)benzene ([$^{18}$F]4)

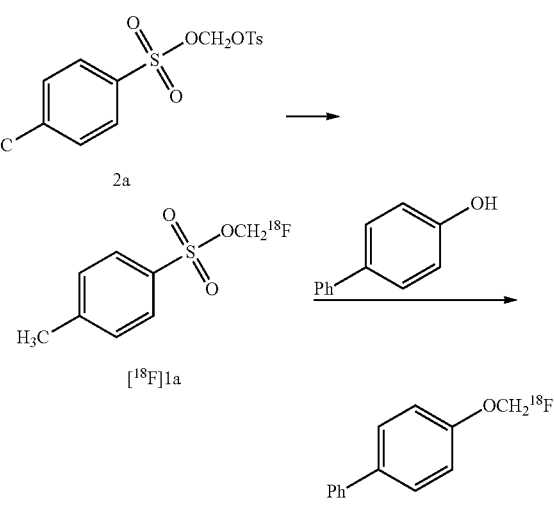

The synthesis of [$^{18}$F]fluoromethyltosylate was followed by an azide substitution reaction (nBu$_4$NN$_3$), immediately after which 0-[$^{18}$F]fluoromethylation was performed. After completion of the reaction, a radio-TLC scanner was used to determine the radiochemical conversion yield. The resultant mixture was subjected to HPLC separation under the conditions of acetonitrile/water (v/v=60/40) ($T_R$=15.3 min for [$^{18}$F]4). The product thus obtained was separated on a cartridge packed with tC18-substituted silica to obtain the final compound.

<Preparation Example 7> Preparation of tert-Butyl (R)-2-((tert-butoxycarbonyl)amino)-3-(4-([$^{18}$F]fluoromethoxy)phenyl)propanoate analogs ([$^{18}$F]6a-b)

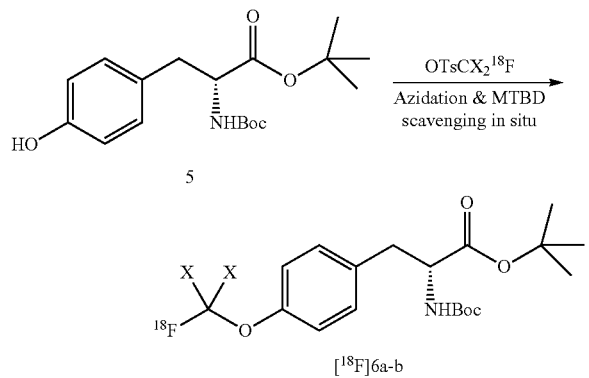

The synthesis of [$^{18}$F]fluoromethyltosylate was followed by adding nBu$_4$NN$_3$ for an azide substitution reaction to cause a reaction at 40 to 100° C. for 2 to 10 minutes. A cartridge packed with C18-substituted silica was used to separate [$^{18}$F]fluoromethyltosylate ([$^{18}$F]1a-b) from the crude mixture. Then, ter-butyl(tert-butoxycarbonyl)-D-tyrosinate, cesium carbonate, and 1,4,7,10,13,16-hexaoxacyclooctadecane dissolved in acetonitrile were added to the separated compound to cause a reaction at 50 to 150° C. for 5 to 15 minutes. After completion of the reaction, the crude mixture was cooled down to the room temperature and MTBD (20 mL) was added. After agitation at 0 to 80° C. for 1 to 10 minutes, the crude mixture was subjected to a separation on a silica Sep-Pak cartridge and another separation on a cartridge packed with C18-substituted silica.

<Preparation Example 8> Preparation of [$^{18}$F]fluoromethyl-dimethyl-2-hydroxyethylammonium ([$^{18}$F] Fluorocholine)

According to the present invention, the synthesis of [$^{18}$F]fluoromethyltosylate was followed by adding nBu$_4$NN$_3$ for an azide substitution reaction to cause a reaction at 40 to 100° C. for 2 to 10 minutes. A cartridge packed with C18-substituted silica was used to separate [$^{18}$F]fluoromethyltosylate ([$^{18}$F]1a-b) from the crude mixture. Then, 2-dimethylaminoethanol dissolved in a mixed solution of acetonitrile and water was added to the separated compound to cause a reaction at 50 to 150° C. for 5 to 15 minutes. After completion of the reaction, the crude mixture was cooled down to the room temperature and separated on an ion exchange cartridge.

Although the exemplary embodiments of the present invention have been described with reference to limited embodiments and drawings, it is understood that the present invention should not be limited to these exemplary embodiments but various changes and modifications can be made by one ordinary skilled in the art.

Accordingly, the scope of the present invention is not limited to these embodiments, but it should be defined by the following claims and equivalents to the claims.

INDUSTRIAL AVAILABILITY

The present invention relates to a method for preparing a fluorine-18-labeled fluoromethyl-substituted radiopharmaceutical using a selective azide substitution reaction that comprises: (1) obtaining a [$^{18}$F]fluoride from a cyclotron through an $^{18}$O (p,n)$^{18}$F reaction; (2) separating the [$^{18}$F] fluoride using an acetonitrile reaction solution containing dissolved K$_{2,2,2}$ and K$_2$CO$_3$ to obtain a [$^{18}$F]F$^-$/H$_2$$^{18}$O solution; (3) heating the [$^{18}$F]F$^-$/H$_2$$^{18}$O solution to obtain K$_{2,2,2}$/K$^{18}$F; (4) placing the K$_{2,2,2}$/K$^{18}$F along with a bis(tosyloxy)methane compound into a reactor and adding a reaction solvent to cause a reaction and obtain a first precursor solution; (5) cooling the first precursor solution and adding an azide reagent to cause an azide substitution reaction and obtain a [$^{18}$F]fluoromethyltosylate compound; (6) adding a bioactive molecule to the [$^{18}$F]fluoromethyltosylate compound to cause an alkylation reaction and obtain a second precursor solution; and (7) adding a precursor scavenger to the second precursor solution and scavenging unreacted precursors to produce a fluorine-18-labeled fluoromethyl-substituted radiopharmaceutical.

According to the present invention, the synthesis process of a radiopharmaceutical involves using a selective azide substitution reaction to inactivate the excess bis(toxyloxy) methane compound present in a crude mixture and significantly increasing the yield of alkylation of a bioactive molecular precursor and the [$^{18}$F]fluoromethyltosylate compound in the subsequent step, to produce a fluorine-18-labeled fluoromethyl-substituted radiopharmaceutical with high radiochemical purity though avoiding a HPLC separation and purification process, thereby reducing the manufacturing time and cost caused by the HPLC process.

What is claimed is:

1. A method for preparing a [$^{18}$F]fluoromethyl-substituted radiopharmaceutical using a selective azide substitution reaction, comprising:
   (1) performing a fluorine-18 labeling reaction of bis (tosyloxy)methane and obtaining a first precursor solution containing [$^{18}$F]fluoromethyltosylate;
   (2) adding an azide reagent to the first precursor solution to cause an azide substitution reaction selectively on unlabeled bis(tosyloxy)methane compound present in the first precursor solution; and
   (3) adding a bioactive molecule to the [$^{18}$F]fluoromethyltosylate compound and obtaining a second precursor solution containing a [$^{18}$F]fluoromethyl-substituted radiopharmaceutical.

2. The method of claim 1, wherein the step (1) of obtaining the first precursor solution is performed by placing the K$_{2,2,2}$/K$^{18}$F along with a bis(tosyloxy)methane compound into a reactor and adding a reaction solution to cause a reaction at 80 to 180° C. for 1 to 30 minutes.

3. The method of claim 2, wherein the K$_{2,2,2}$/K$^{18}$F is obtained by the following steps:
   obtaining a [$^{18}$F]fluoride from a cyclotron through an $^{18}$O (p,n)$^{18}$F reaction;
   separating the [$^{18}$F] fluoride using an acetonitrile reaction solution containing dissolved K$_{2,2,2}$ and K$_2$CO$_3$ to obtain a [$^{18}$F]F$^-$/H$_2$$^{18}$O solution; and
   heating the [$^{18}$F]F$^-$/H$_2$$^{18}$O solution to obtain K$_{2,2,2}$/K$^{18}$F.

4. The method of claim 1, wherein the azide substitution reaction is performed at 40 to 100° C. for 2 to 10 minutes.

5. The method of claim 1, wherein the step (2) further includes performing a cartridge separation process using a cartridge packed with C18-substituted silica to separate the [$^{18}$F]fluoromethyltosylate compound or moving the first precursor solution on to the step (3) without the cartridge separation process.

6. The method of claim 1, wherein O, N, S or P alkylation reaction occurs in the [$^{18}$F]fluoromethyltosylate compound by adding the bioactive molecule in the step (3).

7. The method of claim 1, the method further comprises (4) adding a precursor scavenger to the second precursor solution and scavenging unreacted precursors,
 wherein the precursor scavenger is a scavenger selected from the group consisting of guanidine-based heterocycles and isocyanates.

8. The method of claim 1, wherein the method is performed on an automated synthesis device and a cassette system.

* * * * *